(12) United States Patent
Hung

(10) Patent No.: US 8,794,966 B2
(45) Date of Patent: *Aug. 5, 2014

(54) DENTAL IMPLANT FIXTURE MOUNT-ABUTMENT AND BALL IMPRESSION SCREW

(76) Inventor: William Hung, Claremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/387,947

(22) Filed: May 9, 2009

(65) Prior Publication Data
US 2010/0285427 A1    Nov. 11, 2010

(51) Int. Cl.
*A61C 8/00* (2006.01)

(52) U.S. Cl.
USPC .......................................... 433/174; 433/173

(58) Field of Classification Search
USPC ............... 433/172–176, 201.1; 411/484, 486, 411/500, 507; 606/300, 301–320
See application file for complete search history.

(56) References Cited

U.S. PATENT DOCUMENTS

| | | | | |
|---|---|---|---|---|
| 5,709,547 A * | 1/1998 | Lazzara et al. | ................ | 433/174 |
| 5,782,918 A * | 7/1998 | Klardie et al. | ................ | 606/60 |
| 7,785,107 B2 * | 8/2010 | Niznick | ................ | 433/173 |
| 8,038,442 B2 * | 10/2011 | Hurson | ................ | 433/173 |
| 2003/0224327 A1 * | 12/2003 | Constantino | ................ | 433/165 |
| 2005/0019730 A1 * | 1/2005 | Gittleman | ................ | 433/174 |
| 2005/0136379 A1 * | 6/2005 | Niznick | ................ | 433/173 |
| 2005/0214714 A1 * | 9/2005 | Wohrle | ................ | 433/173 |
| 2006/0078847 A1 * | 4/2006 | Kwan | ................ | 433/174 |
| 2006/0172257 A1 * | 8/2006 | Niznick | ................ | 433/173 |
| 2007/0059666 A1 * | 3/2007 | Zickman et al. | ................ | 433/173 |
| 2008/0153062 A1 * | 6/2008 | Beaty et al. | ................ | 433/173 |
| 2009/0305191 A1 * | 12/2009 | Jandali | ................ | 433/174 |
| 2010/0248180 A1 * | 9/2010 | Bondar | ................ | 433/141 |
| 2011/0117522 A1 * | 5/2011 | Verma et al. | ................ | 433/174 |

* cited by examiner

*Primary Examiner* — Yogesh Patel
(74) *Attorney, Agent, or Firm* — Raymond Y. Chan; David and Raymond Patent Firm

(57) ABSTRACT

A dental implant fixture mount-abutment includes a fixture mount having a coronal end and an internal slot, a tapered cylinder body, a root for internally connecting to a dental implant, and a plurality of engaging jaws protruded from the root for engaging with an internal channel of the dental implant, such that the root forms a male connector for inserting into the internal channel in the dental implant to stabilize the DIFMA in position.

3 Claims, 10 Drawing Sheets

DENTAL IMPLANT FIXTURE MOUNT-ABUTMENT AND BALL IMPRESSION SCREW

BACKGROUND OF THE PRESENT INVENTION

1. Field of Invention

The present invention relates to (1) a dental implant fixture mount-abutment (DIFMA), particularly to the DIFMA having (a) a fixture mount and (b) an abutment with internal (triangular, square, pentagonal or hexagonal) slots for a fixture mount driver to place a dental implant and the DIFMA simultaneously, (2) a ball impression screw (BIS) for making an impression immediately after implant surgery, and (3) a fixture mount driver having a latch type end/square type end, driver shank and body to torque a DIFMA by inserting into the driven channel of the DIFMA during placement of a dental implant and a DIFMA into alveolar bone.

2. Description of Related Arts

Traditionally, a fixture mount (FM) has been used by most of dental implant systems to deliver and place dental implants. After the dental implant placed, the FM is removed from the dental implant and is discarded. Three to six months after the dental implant placed, a conventional impression coping and copping screw are used for the purpose of making an impression to fabricate a stone cast for restoration which is not only a time consuming process but a waste of material due to discarding the FM.

Therefore, in order to provide a dental restoration, dentists have to pay the cost of the FM, impression copping/copping screw, preformed or custom abutment, which can be expensive, time consuming and clinical inconvenience.

The new design of the DIFMA is compelling because it can reduce cost, improve patient comfort and reduce clinical chair time/treatment time. The present invention which is a new design can be used as a FM, impression copping, provisional abutment and/or permanent abutment. In other word, a device can be used for four (4) purposes. This new design includes a DIFMA, a BIS and a fixture mount driver.

The DIFMA can be used as a FM, impression copping, temporary and/or permanent abutment. The BIS can be placed on the top of the new designed DIFMA to secure the DIFMA immediately after the dental implant placed and impression can be made immediately after the dental implant surgery without waiting period to facilitate an immediate loading of restoration. Patients can receive the benefits of chewing function and esthetics, immediately after the dental implant surgery, without a waiting period of three to six months.

SUMMARY OF THE PRESENT INVENTION

A main object of the present invention is to provide a DIFMA which is cost effective and is less expensive.

Another object of the present invention is to provide a DIFMA which reduces time of treatment (chair time).

Another object of the present invention is to provide a DIFMA which reduces waiting period of treatment (three to six months).

Another object of the present invention is to provide a DIFMA which can improve clinical convenience. (It is difficult to seat impression copping immediately after the dental implant surgery due to bleeding)

Another object of the present invention is to provide a DIFMA which can reduce office visits.

Another object of the present invention is to provide a DIFMA which facilitates/speeds the process of immediate loading for function and esthetic reasons.

Another object of the present invention is to provide a DIFMA which can increase patient comfort.

Another object of the present invention is to provide a BIS which provides additional surface for indentation/indexing can improves accuracy of impression.

Another object of the present invention is to provide a BIS which is cost effective and is less expensive.

Another object of the present invention is to provide a BIS which reduces time of treatment (chair time).

Another object of the present invention is to provide a BIS which can improve clinical convenience. (It is difficult to seat impression copping immediately after a dental implant surgery due to bleeding)

Another object of the present invention is to provide a BIS for making an impression immediately after the dental implant surgery.

Accordingly, in order to accomplish the above objects, the present invention provides a dental implant fixture mount-abutment and a ball impression screw, comprising:

a fixture mount serves as an impression coping;

two small flat facets of the fixture mount for providing an anti-rotation feature;

a circumferential groove of the DIFMA;

an abutment;

two large flat facets of the abutment for providing an anti-rotation feature;

a shoulder of the abutment;

a circumferential curvature of the abutment;

a root for internally connecting to the dental implant;

three engaging jaws protruded from the root for inserting and engaging in the internal channel of the dental implant;

an internal hexagonal (or triangular, square, pentagonal) slot for receiving a hexagonal (or triangular, square, pentagonal) fixture mount driver;

a coronal head of the BIS;

a bolt of the BIS;

an apical end of the BIS for inserting into the DIFMA and the dental implant; securing the DIFMA and the dental implant;

These and other objectives, features, and advantages of the present invention will become apparent from the following detailed description, the accompanying drawings, and the appended claims.

DETAILED DESCRIPTION OF THE PREFERRED EMBODIMENT

Figure 1:
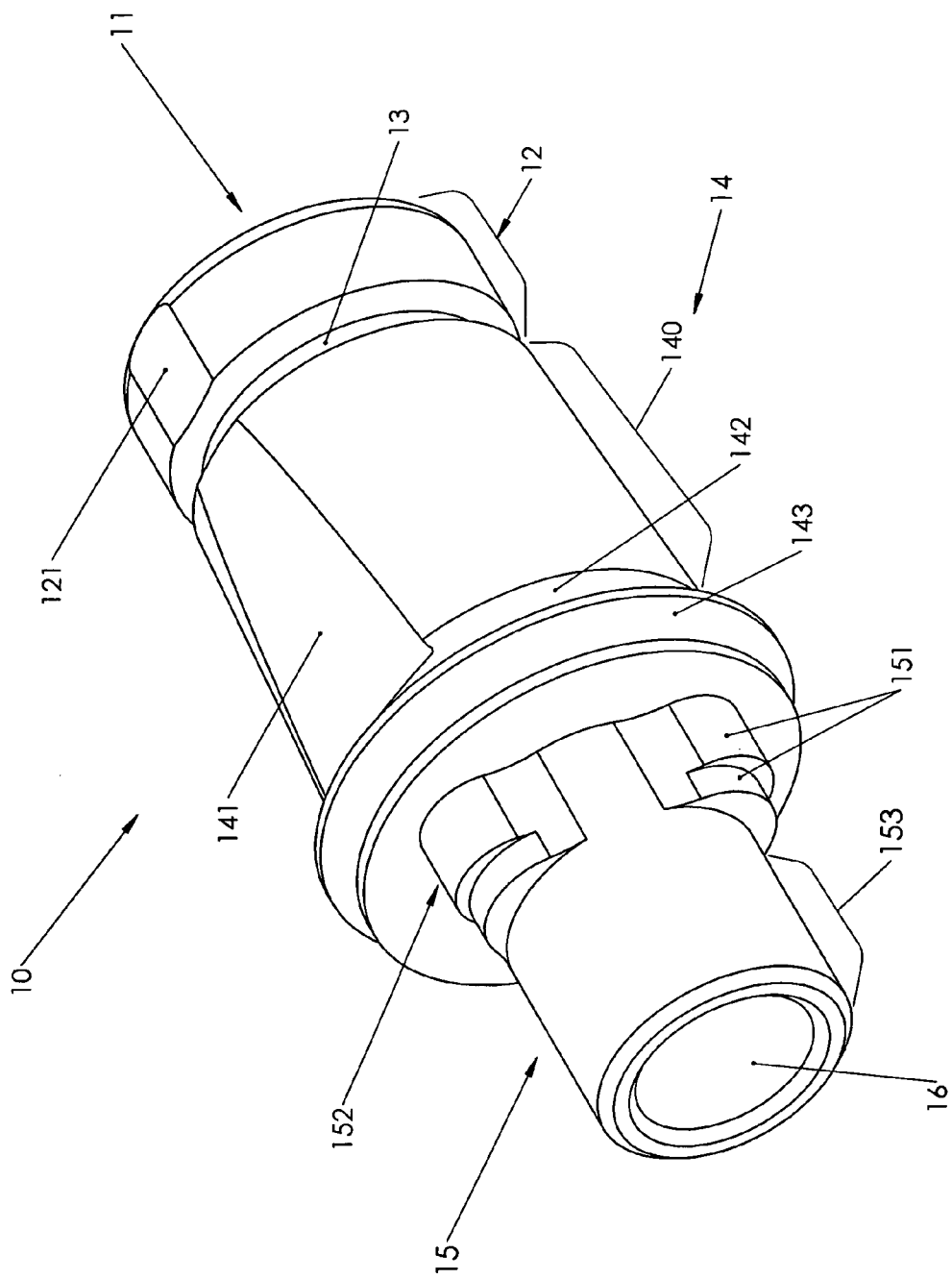
FIG. 1 is a perspective view of a dental implant fixture mount-abutment (DIFMA) according to a preferred embodiment of the present invention.

Referring to FIGS. 1 to 5 of the drawings, a dental implant fixture mount-abutment (DIFMA) 10 according to a preferred embodiment of the present invention is illustrated, wherein the DIFMA 10 comprises a fixture mount 12, which is a metal collar at a coronal end 11 for receiving a fixture mount driver 30, an abutment 14, which is a tapered cylinder body 140, and a root 15, which is a cylinder body 153, for internally connecting to a dental implant 70 through a bolt 50. The bolt 50 is used to secure the DIFMA 10 and the dental implant 70 before using the fixture mount driver 30.

The fixture mount 12 is a 2 to 7 mm coronal extension/ metal collar delineated from the abutment portion 14 separated by a circumferential groove 13. The fixture mount 12 is designed to extend the DIFMA 10 with the addition of the ball impression screw (BIS) 90 to serve as an impression coping for closed tray technique. The abutment 14 can be used as a temporary abutment after the fixture mount 12 is removed by a lab disk. The circumferential groove 13 is also designed to serve as an impression coping retentive feature. As illustrated in the cross sectional view of FIG. 3, a driven channel 112 of the coronal end 11 of the DIFMA 10 is designed to receive the fixture mount driver 30.

The fixture mount 12 has two small flat facets 121, located at opposite sites of the fixture mount 12, extending between the coronal end 11 and the circumferential groove 13. The abutment 14 has a tapered cylinder body 140 with two large flat facets 141, located at opposite sites of the abutment 14, extending between the circumferential groove 13 and the shoulder 142. The small flat facets 121 and the large flat facets 141 enable the DIFMA 10 to provide an anti-rotation feature for crown restoration.

Figure 3:
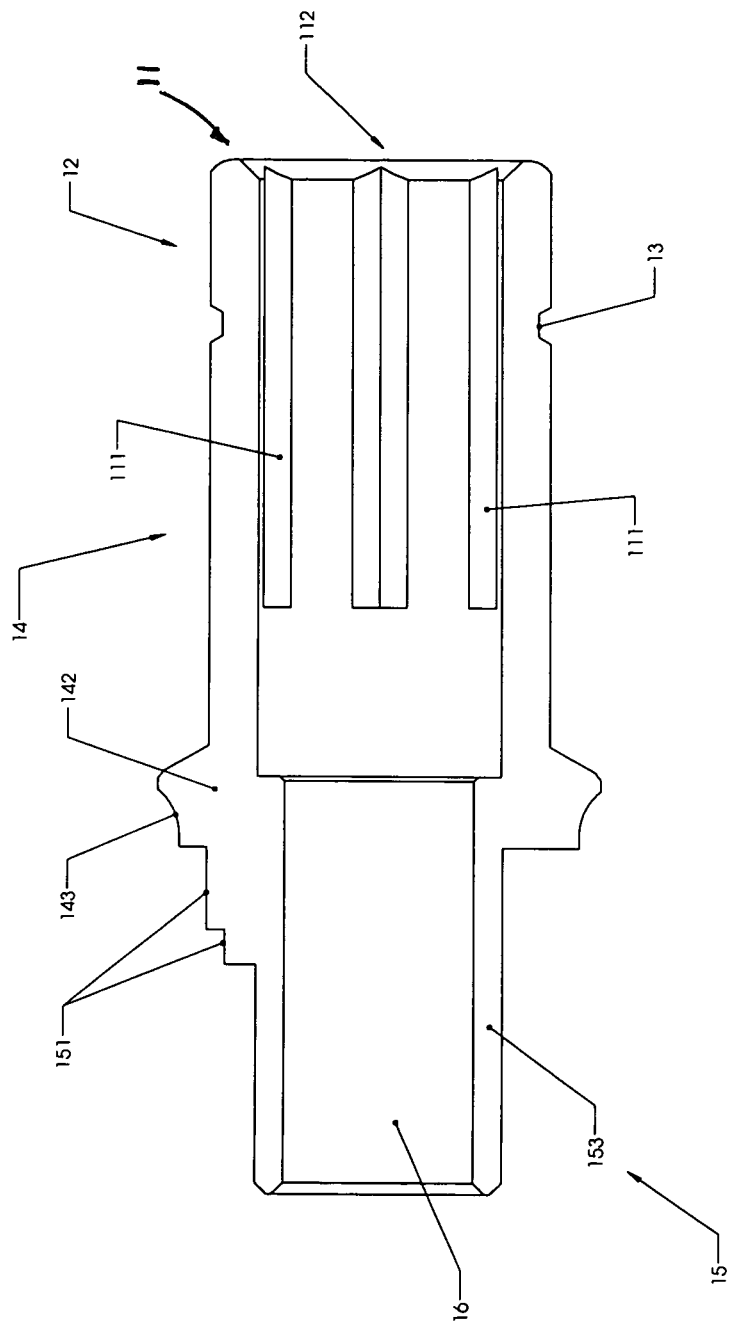
FIG. 3 is a sectional view of the DIFMA according to above preferred embodiment of the present invention.

Referring to FIG. 3, the DIFMA 10 has a shoulder 142 on the abutment portion 14. The shoulder 142 is designed to seat the margin of a crown restoration. A circumferential curvature 143 apically located to the shoulder 142 is designed to avoid engaging alveolar bone so as to be easily removed later.

Referring to FIG. 1, the root 15 of the DIFMA 10 is a male connector for internally connecting to the dental implant 70. The root 15 is designed to be inserted into the dental implant 70 and the root 15 is fit to an internal channel 71 of the dental implant 70. The diameter of the abutment 14 and the root 15 varies according to different sizes of the dental implant 70.

The root 15 of the DIFMA 10 has three engaging jaws 152 protruding from the root 15. Each of jaw 152 has two stairs 151. The three jaws 152 of the root 15 are located between the circumferential curvature 143 and a cylinder body 153 of the root 15 and are located 120° apart from each other and adapted to engage the internal channel 71 in the dental implant 70. The jaws 152 are designed to provide anti-rotation and friction to stabilize the DIFMA 10 with the dental implant 70 by inserting into the female slots of the dental implant 70. When the engaging jaws 152 are inserted and engaged in the internal channel 71 of the dental implant 70, the position of the DIFMA 10 is secured and the rotation of the DIFMA 10 is prevented.

Figure 2:
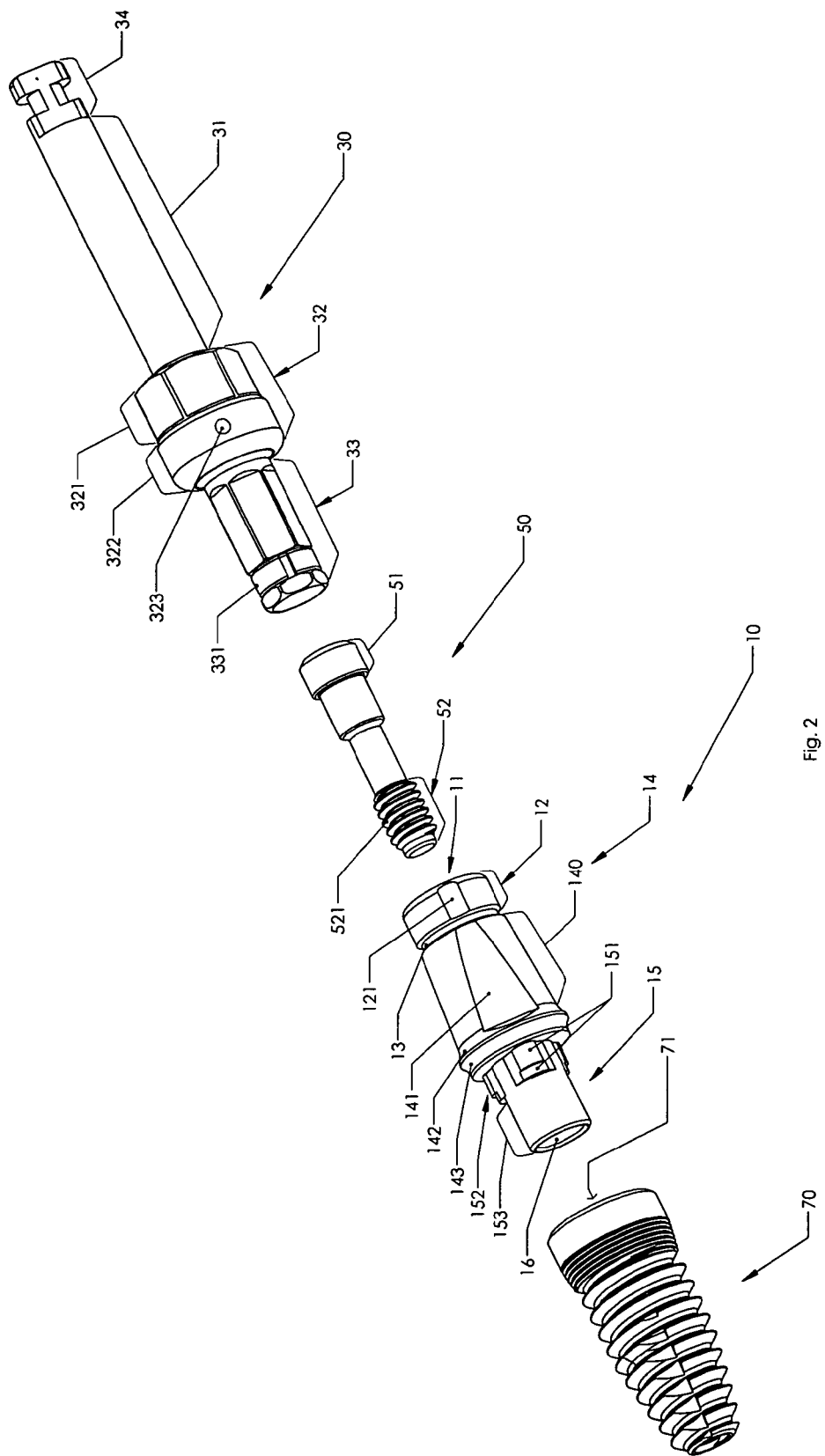
FIG. 2 is an exploded view illustrating a dental implant, a DIFMA, a bolt and a fixture mount driver for securing the abutment with the dental implant according to above preferred embodiment of the present invention.

Referring to FIG. 2, the DIFMA 10 is fastened onto the dental implant 70 through the bolt 50. The DIFMA has a through hole 16 communicating the internal channel 71 of the dental implant 70.

Referring to FIG. 2, a tip 52 of the bolt 50 having an external thread 521 is adapted to pass through the through hole 16 of the DIFMA 10 and the internal channel 71 of the dental implant 70. A head 51 of the bolt 50 remains in the through hole 16 of the DIFMA 10 for driving the bolt 50 and retaining the abutment 14. In this manner, the bolt 50 and the dental implant 70 have a metal to metal contact which is very stable. This can steadily fasten the abutment 14 onto the dental implant 70. The stability is largely increased.

Figure 4:
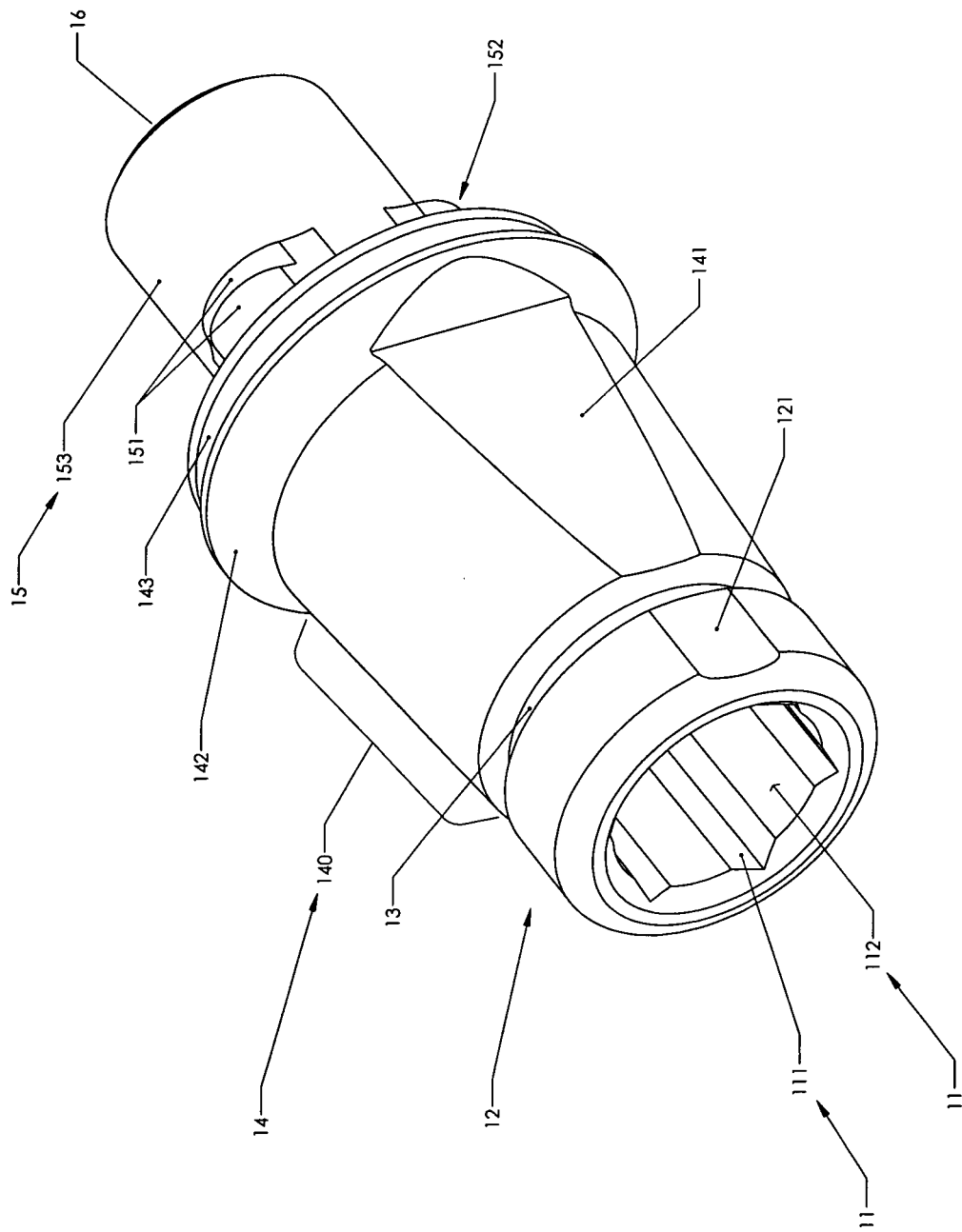
FIG. 4 is a perspective view of an alternative mode of the DIFMA according to above preferred embodiment of the present invention.
Figure 5:
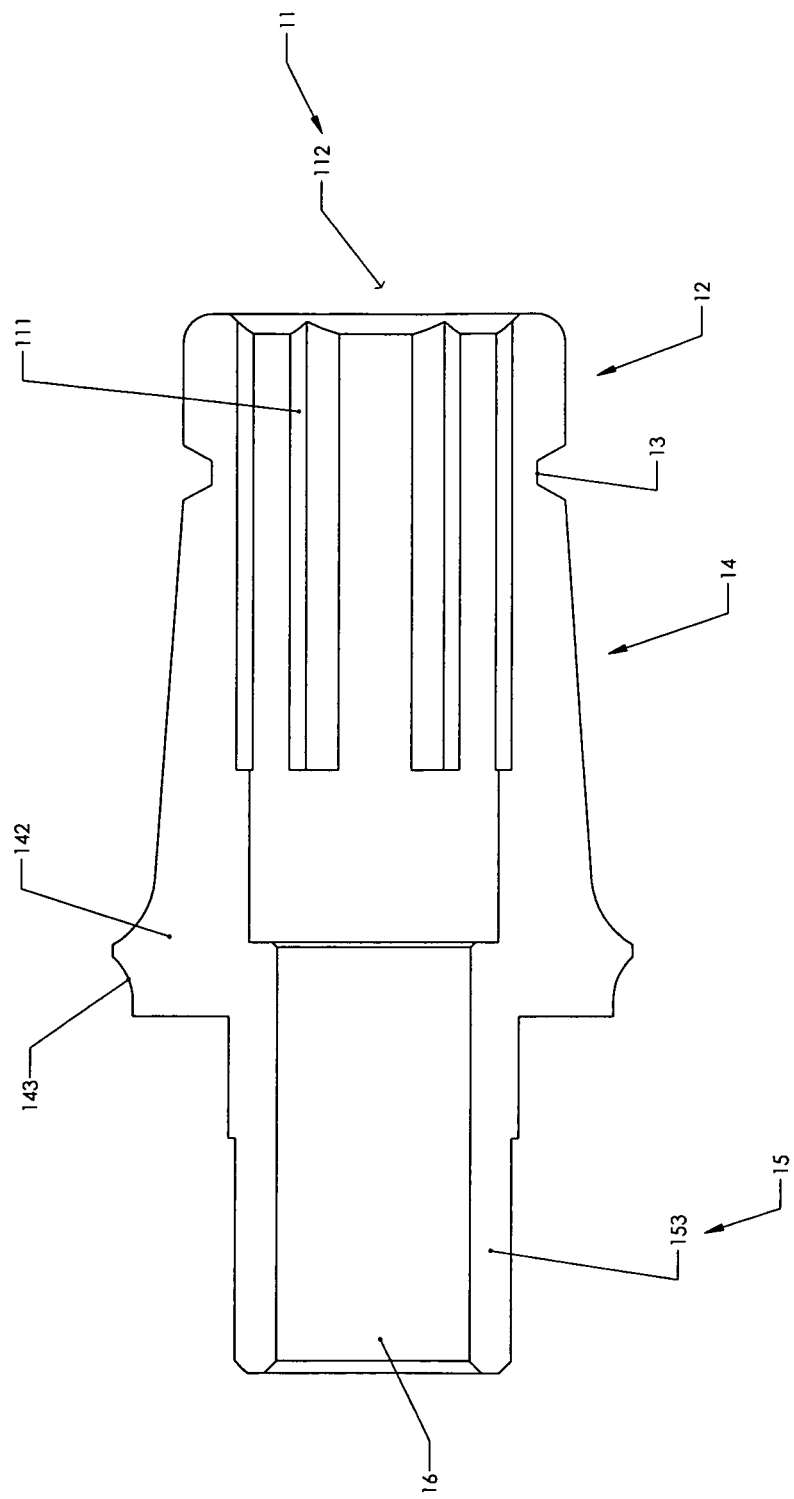
FIG. 5 is a section view of the alternative mode of the DIFMA according to above preferred embodiment of the present invention.
Figure 6:
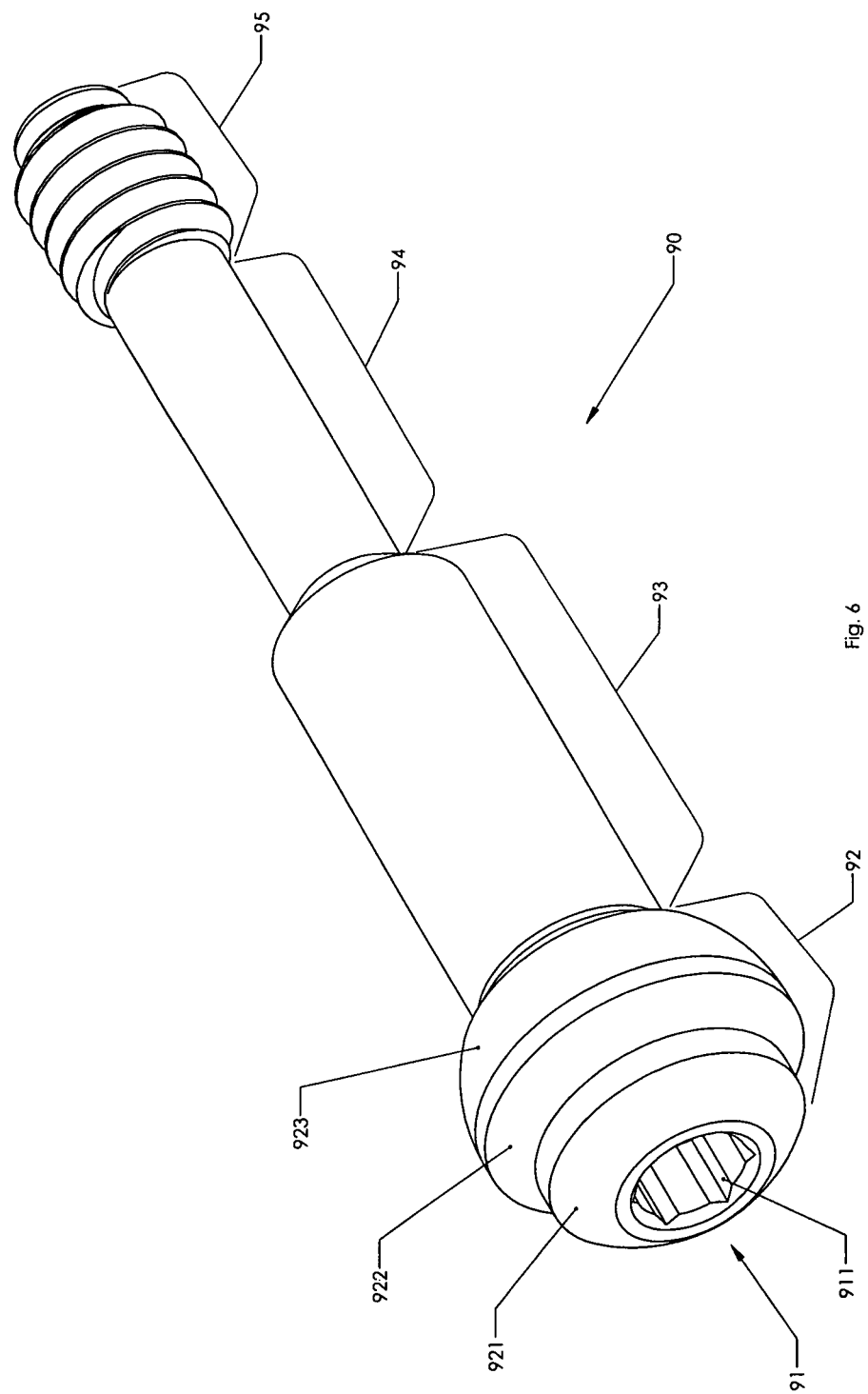
FIG. 6 is a perspective view of the ball impression screw (BIS) according to above preferred embodiment of the present invention.
Figure 7:
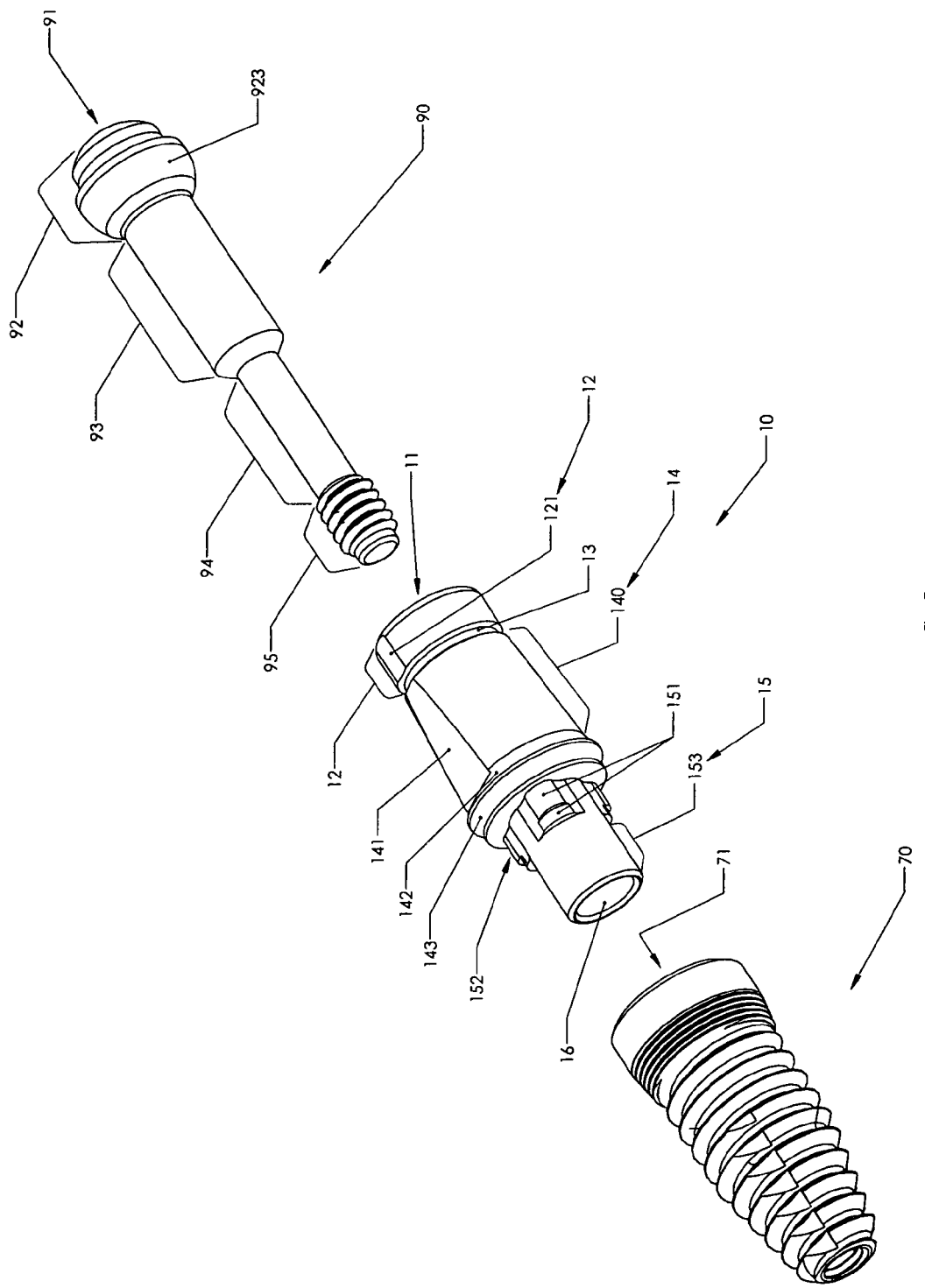
FIG. 7 is an exploded view illustrating a dental implant, a DIFMA and a BIS for securing the abutment with the dental implant according to above preferred embodiment of the present invention.
Figure 8:
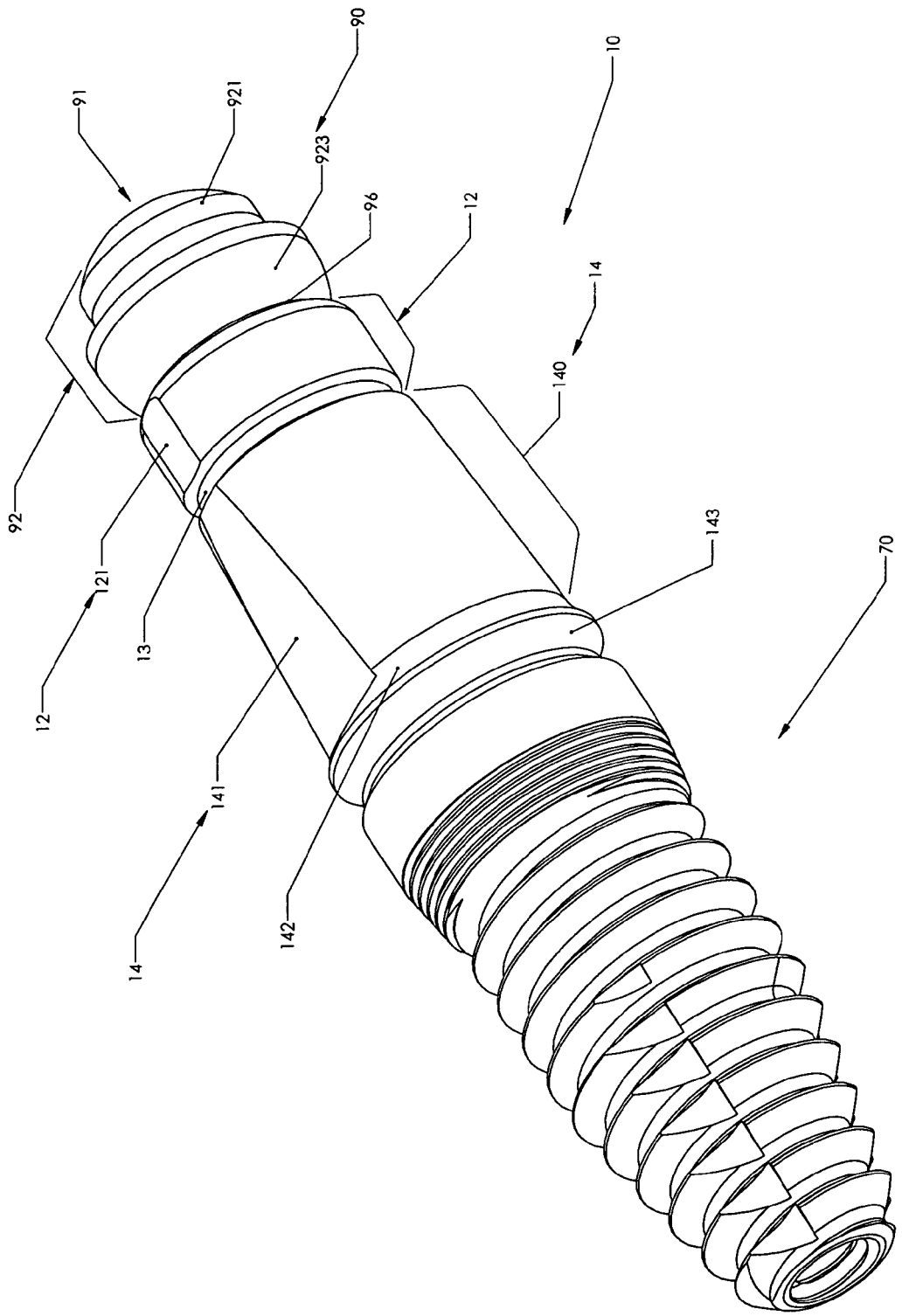
FIG. 8 is a connected view illustrating a dental implant, a DIFMA and a BIS for securing the abutment with the dental implant according to above preferred embodiment of the present invention.
Figure 9:
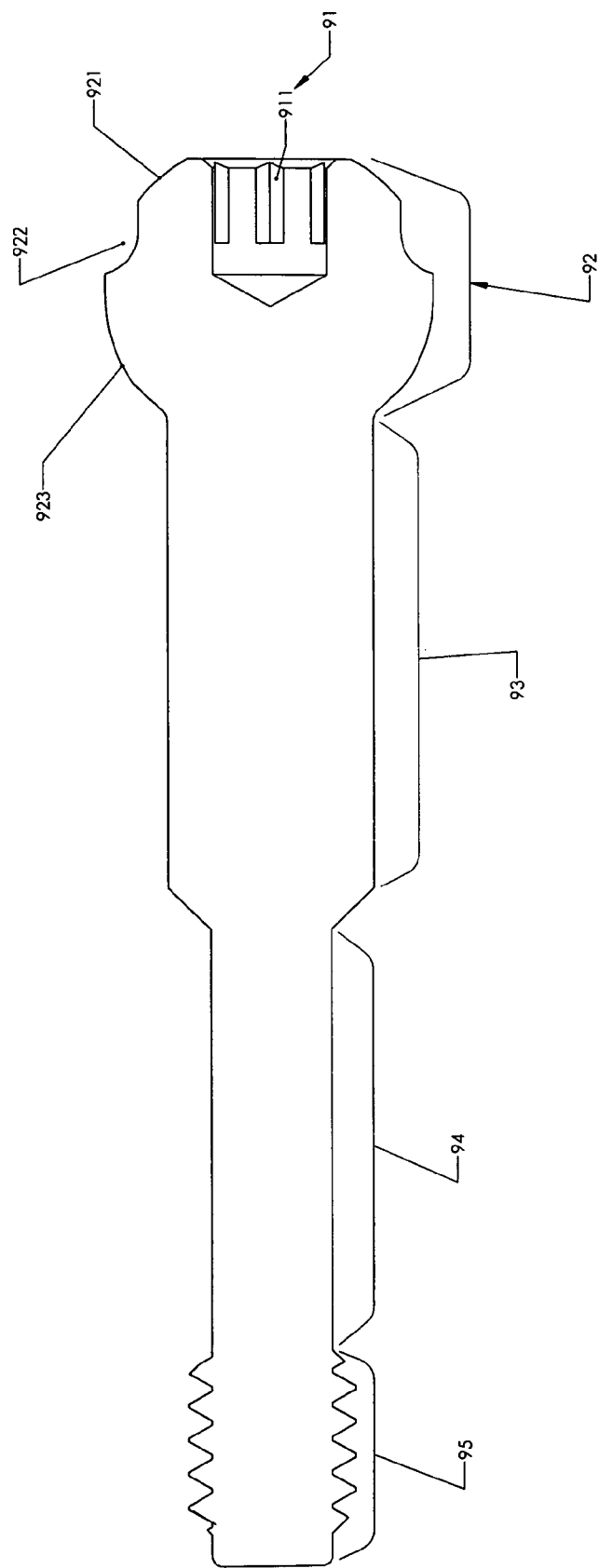
FIG. 9 is a sectional view of the BIS according to above preferred embodiment of the present invention.
Figure 10:
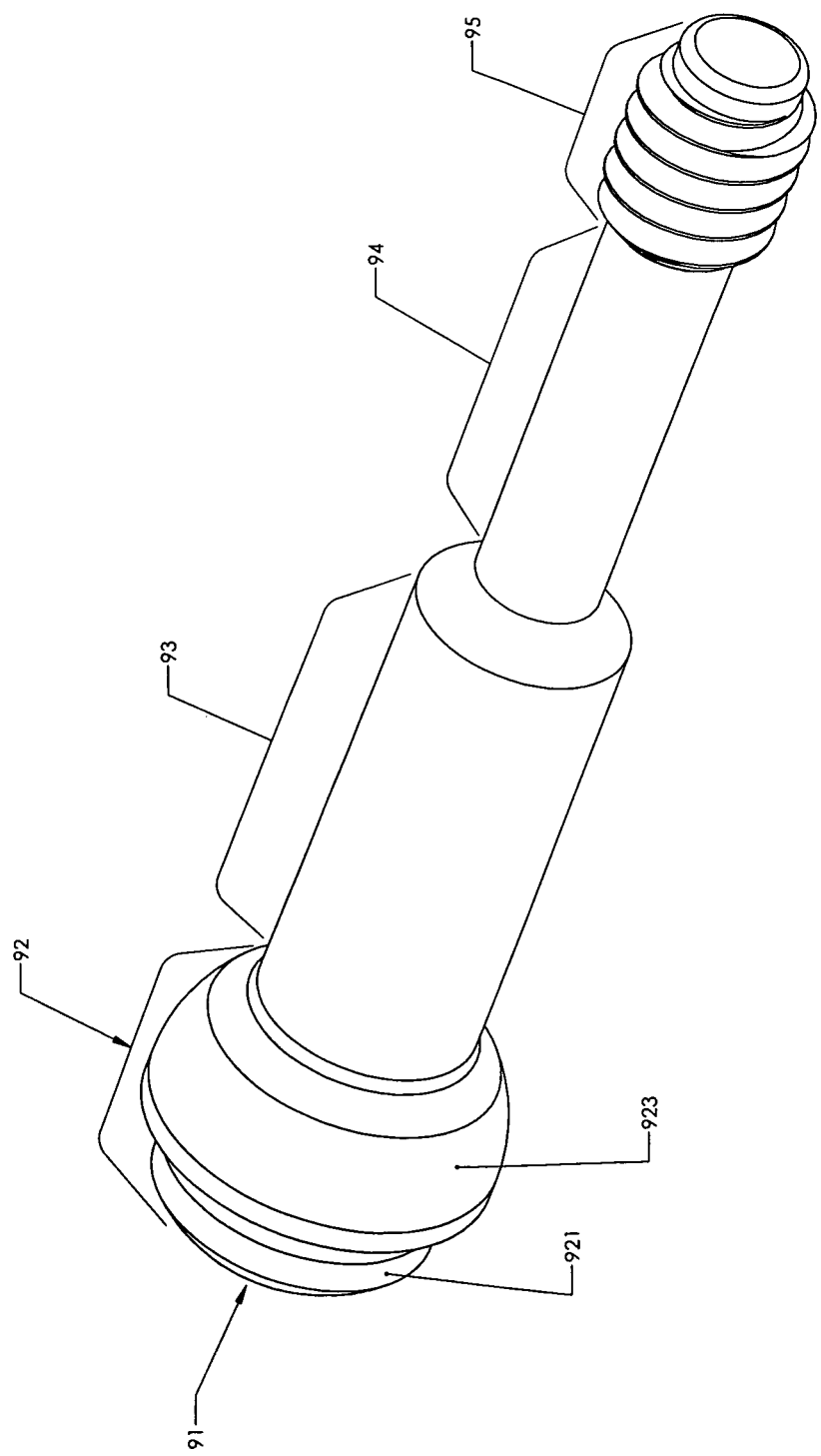
FIG. 10 is a perspective view of an alternative mode of the BIS according to above preferred embodiment of the present invention.

Referring to FIGS. 3 to 5 of the drawings, an internal hexagonal (triangular, square or pentagonal) slot 111 located at the internal wall of the DIFMA 10 is designed to receive the hexagonal (triangular, square or pentagonal) fixture mount driver 30. The length of the slots 111 can rang from 4 mm to 8 mm.

Referring to FIG. 2, the fixture mount driver 30, according to a preferred embodiment of the present invention are illustrated, wherein the fixture mount driver 30 comprises a shank 31, which is a cylinder body, a latch type end 34, for adapting to a slow speed hand piece, a hex body 32, having a upper hexagonal body 321 and a round lower body 322 with color coding 323 and a hex cylinder shank 33 with a plastic O ring 331 on the end to carry the DIFMA 10 and to place the dental implant 70.

Referring to FIGS. 6 to 10 of the drawings, the ball impression screw (BIS) 90, according to a preferred embodiment of the present invention, is illustrated, wherein the BIS 90 comprises a dental implant ball impression screw bolt 94, which is a cylinder body, having the apical end 95 for inserting through the DIFMA 10 into the dental implant 70 and a dental implant ball impression screw shank 93, which is a cylinder body, having the coronal head 92 for providing additional retentive feature for the DIFMA 10 to serve as an impression coping.

After the dental implant 70 is placed, the fixture mount driver 30 and the bolt 50 used to fasten the DIFMA 10 onto the dental implant 70 are removed. Then, the BIS 90 is used to connect and fasten the DIFMA 10 onto the dental implant 70. A coronal head 92 of the BIS 90 remains outside of the driven channel 112 of the DIFMA 10.

Referring to FIGS. 6 to 9, the coronal head 92 of the shank 93 comprises a large hemisphere 923, a circumferential notch 922, a small hemisphere head 921 and a hexagonal concavity 91. The connection between the large hemisphere 923 and the fixture mount 12 will form a circumferential groove 96 to serve as an impression coping retentive feature. An internal hexagonal (or triangular, square, pentagonal) slot 911 of the hexagonal concavity 91 is made to receive the hexagonal (or triangular, square, pentagonal) fixture mount driver 30.

In summary, the DIFMA 10 specifically designed for the purpose of immediate implant placement and immediate impression taking was proposed. The new design employs several modern concepts in order not only to enhance the primary stability but also to provide multiple applications of an implant fixture mount. Utilizing the new designed DIFMA 10 coupled with the BIS 90, the clinician can take an immediate final impression right after implant placement. A cast can then be immediately poured for wax up and a screw-retained/cement retained provisional prosthesis is fabricated and delivered within the same day. A definitive prosthesis can be fabricated and delivered in a couple of days. Alternatively, an acrylic shell can be fabricated before the surgery and a provisional prosthesis can be fabricated and placed on the modified DIFMA 10 to be used as a temporary abutment at chair side right after the dental implant placement. The DIFMA 10 can also be modified and used as a permanent abutment.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

A fixture mount driver, comprising a shank which is a cylinder body having a latch type end, a body which has a upper hexagonal body and a round lower body with color coding and a hex cylinder shank with a plastic O ring on the end.

What is claimed is:

1. A dental implant arrangement, comprising:
   a bolt having a tip and an external thread;
   a fixture mount driver which comprises a cylindrical shank, a latch type end which is provided at one end of said shank, a hex body which is provided at another end of said shank having an upper hexagonal body and a round lower body, and a hex cylinder shank for carrying said dental implant fixture mount-abutment and to place the dental implant in position;
   a dental implant fixture mount-abutment, which comprises:
   a root provided at one end of said abutment wherein said root has a cylinder body having a size smaller than said cylinder body of said abutment, wherein said root is a male connector for internally connecting to a dental implant by inserting into an internal channel of the dental implant through the bolt which is used to secure said dental implant fixture mount-abutment and the dental implant before using the fixture mount driver;
   a shoulder provided on said abutment adjacent to said root, wherein said shoulder is provided to seat a margin of a crown restoration wherein a circumferential curvature is apically located to said shoulder for avoiding engaging alveolar bone for easily removing; and
   a fixture mount provided at the other end of said abutment, wherein said fixture mount is a collar forming a coronal end of said dental implant fixture mount-abutment for receiving the fixture mount driver, wherein said fixture mount has a length of 2 to 7 mm coronal extension collar delineated from said abutment wherein a circumferential groove is provided between said abutment and said fixture mount to serve as an impression coping retentive feature, wherein said fixture mount has a driven channel at said coronal end of said dental implant fixture mount-abutment for receiving said fixture mount driver, wherein said fixture mount has two small flat facets located at opposite sites thereof and extended between said coronal end and said circumferential groove, wherein said two large flat facets of said abutment, extended between said circumferential groove and said shoulder of said abutment and said two small flat facets of said fixture mount enable said dental implant fixture mount-abutment to provide an anti-rotation feature for crown restoration, wherein said coronal end of said dental implant fixture mount-abutment has an internal slot, having a length of 4 to 8 mm, located at an internal wall thereof for receiving the fixture mount driver; and
   a ball impression screw which comprises a dental implant ball impression screw bolt, which is a cylinder bolt body, having an apical end for inserting through said dental implant fixture mount-abutment into the dental implant and a dental implant ball impression screw shank, which is a cylinder shank body, having a coronal head for providing additional retentive feature for said dental implant fixture mount-abutment to serve as an impression coping, wherein said fixture mount is capable of extending said dental implant fixture mount-abutment with an addition of the ball impression screw to serve as the impression coping for closed tray technique so that said abutment is able to be used as a temporary abutment after said fixture mount is removed, wherein after the dental implant is placed in position, the fixture mount driver and said bolt which are used to fasten said dental implant fixture mount-abutment onto the dental implant are removed, and then, said ball impression screw is used to connect and fasten said dental implant fixture mount-abutment onto the dental implant, while said coronal head of the ball impression screw remains outside of said driven channel of said dental implant fixture mount-abutment, wherein said coronal head of said dental implant ball impression screw shank comprises a large hemisphere, a circumferential notch, a small hemisphere head, and a concavity, wherein a connection between said large hemisphere and a fixture mount forms a circumferential groove to serve as the impression coping retentive feature, wherein said concavity has an internal slot for receiving said fixture mount driver.

2. The dental implant arrangement, as recited in claim 1, wherein said internal slot is selected from the group consisting of hexagonal slot, triangular slot, square slot and pentagonal slot for receiving the fixture mount driver with a corresponding cross section.

3. The dental implant arrangement, as recited in claim 1, wherein said dental implant fixture mount-abutment has a through hole formed at said root for communicating with the internal channel of the dental implant and for enabling the bolt passing through said through hole through said internal slot at a position that a tip of the bolt is inserted into the internal channel of the dental implant while a head of the bolt is remained at said tapered cylinder body of said abutment, wherein said through hole is formed and communicated with said internal slot of said fixture mount.

* * * * *